United States Patent [19]
Brooks et al.

[11] Patent Number: 5,175,183
[45] Date of Patent: Dec. 29, 1992

[54] LIPOXYGENASE INHIBITING COMPOUNDS

[75] Inventors: Dee W. Brooks; James B. Summers; Karen E. Rodriques, all of Libertyville, Ill.

[73] Assignee: Abbott Laboratories, Abbott Park, Ill.

[21] Appl. No.: 721,530

[22] PCT Filed: Jan. 25, 1990

[86] PCT No.: PCT/US90/00376
§ 371 Date: Jul. 10, 1991
§ 102(e) Date: Jul. 10, 1991

Related U.S. Application Data

[63] Continuation-in-part of Ser. No. 305,321, Feb. 1, 1989, abandoned.

[51] Int. Cl.⁵ ............... A61K 31/38; C07D 333/32; C07D 333/22
[52] U.S. Cl. ............... 514/438; 514/445; 514/448; 549/65; 549/76; 549/77; 549/61; 549/72
[58] Field of Search ............... 514/438, 445, 448; 549/65, 76, 77, 61, 72

[56] References Cited

U.S. PATENT DOCUMENTS

| | | | |
|---|---|---|---|
| 4,143,061 | 3/1979 | Kubo et al. | 260/453 |
| 4,339,515 | 7/1982 | Schranz et al. | 430/17 |
| 4,608,390 | 8/1986 | Summers | 514/575 |
| 4,618,692 | 10/1986 | Scheffler et al. | 558/82 |
| 4,623,661 | 11/1986 | Summers | 514/575 |
| 4,728,670 | 3/1988 | Hasianger et al. | 514/484 |
| 4,769,387 | 9/1988 | Summers et al. | 514/468 |
| 4,822,811 | 4/1989 | Summers | 514/411 |
| 4,897,422 | 1/1990 | Summers | 514/575 |
| 5,026,729 | 6/1991 | Brooks et al. | 514/575 |

FOREIGN PATENT DOCUMENTS 0279263 8/1988 European Pat. Off..
0292699 11/1988 European Pat. Off..

Primary Examiner—Alan Siegel
Attorney, Agent, or Firm—Jerry F. Janssen

[57] ABSTRACT

Certain N-aryl, N-heteroaryl-, N-arylalkyl-, N-heteroarylalkyl-, N-arylcyclopropyl- and N-heteroaryl-cyclopropyl-N'-hydroxyurea compounds are inhibitors of lipoxygenase enzyme activity and are thus useful agents in treating disease states such as asthma, arthritis, allergy, psoriasis, inflammatory bowel disease, gout, adult respiratory distress syndrome, endotoxin shock, and other inflammatory conditions in which the products of the arachidonic acid cascade are implicated.

6 Claims, No Drawings

LIPOXYGENASE INHIBITING COMPOUNDS

CROSS-REFERENCE TO RELATED APPLICATIONS

This application is a continuation-in-part of copending U.S. application Ser. No. 305,321 filed Feb. 1, 1989 now abandoned.

TECHNICAL FIELD

This invention relates to compounds which inhibit lipoxygenase enzymes, to pharmaceutical compositions containing these compounds, and to methods of inhibiting lipoxygenase enzymes in human and animal hosts in need of such treatment. More particularly, this invention concerns certain aryl-, arylalkyl- and arylcyclopropyl-N-hydroxyurea compounds which inhibit lipoxygenase enzymes, to pharmaceutical compositions containing these compounds, and to methods of treating disease states mediated by products of the arachidonic acid cascade.

BACKGROUND OF THE INVENTION

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LT's). Similarly 12- and 15-lipoxygenase, convert arachidonic acid to 12- and 15-HPETE respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the $LTC_4$ and $LTD_4$ are potent constrictors of human airways in vitro and aerosol administration of these substances to non-asthmatic volunteers induces broncho-constriction. $LTB_4$ and 5-HETE are potent chemotactic factors for inflammatory cells such as polymorphonuclear leukocytes. They also have been found in the synovial fluid of rheumatoid arthritic patients. The biological activity of the leukotrienes has been reviewed by Lewis and Austin (J. Clinical Invest. 73, 889, 1984) and by Sirois (Adv. Lipid Res. 21, 78, 1985).

Thus, lipoxygenase enzymes play an important role in the biosynthesis of mediators of asthma, allergy, arthritis, psoriasis, inflammatory bowel disease, gout, adult respiratory distress syndrome, endotoxin shock and inflammation. Blocking these enzymes interrupts the biochemical pathways involved in these disease states.

BACKGROUND ART

Relatively few compounds are known from the prior art which are inhibitors of the lipoxygenase enzymes. Among the lipoxygenase inhibitors known to the art are: AA-861, a 5-lipoxygenase inhibitor, disclosed in U.S. Pat. No. 4,393,075, issued Jul. 12, 1983 to Terao et al.; pyrazolo pyridines, which are 5-lipoxygenase inhibitors, disclosed in European Patent Application of Irikura et al., S.N. 121,806, published Oct. 17, 1984; arachidonyl hydroxamic acid, a 5-lipoxygenase inhibitor, disclosed in E. J. Corey et al., J. Am. Chem. Soc., 106, 1503 (1984) and European Patent Application of P. H. Nelson, S.N. 104,468, published Apr. 4, 1984; BW755C, an inhibitor of 5- and 12-lipoxygenases, disclosed in Radmark et al., FEBS Lett., 110, 213 (1980); nordihydro-guariaretic acid, an inhibitor of 5- and 15-lipoxygenases, disclosed in Morris et al., Prostaglandins, 19, (1980); REV-5901, a 5-lipoxygenase inhibitor, disclosed in Coutts, Meeting Abstract 70, Prostaglandins and Leukotrienes '84; quinoline N-oxides, 5-lipoxygenase inhibitors disclosed in European patent application of Hashizumo et al., Ser. No. 128,374, published Dec. 19, 1984 and benoxaprofen, disclosed in J. Walker, Pharm. Pharmacol., 31, 778 (1979).

SUMMARY OF THE INVENTION

The compounds of this invention possess unexpected activity as inhibitors of lipoxygenase enzymes, and reduce the biosynthesis of leukotrienes $B_4$, $C_4$, $D_4$ and $E_4$. The compounds and compositions containing these compounds are useful for the treatment of disease states in mammals, which disease states are mediated by the leukotrienes $B_4$, $C_4$, $D_4$ and $E_4$.

The compounds of this invention have the structural formula, I:

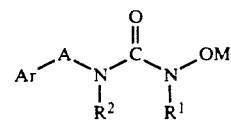

where A is a divalent radical selected from the group consisting of alkylene of from one to six carbon atoms, alkenylene, of from two to twelve carbon atoms, $-(CH_2)_m-O-(CH_2)_n-$ where m and n are independently selected from zero and integers of from one to six, $-O-(CH_2)_m-$ where m is as previously defined, and as divalent group of the structure

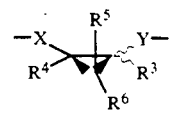

where X is either absent or is divalent alkylene of from one to four carbon atoms, Y is either absent or is divalent alkylene of from one to four carbon atoms, $R^3$ and $R^4$ are independently selected from hydrogen or alkyl, and $R^5$ and $R^6$ are independently selected from hydrogen, alkyl, or halogen.

Ar is selected from the group consisting of

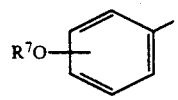

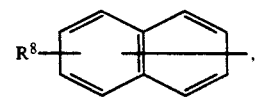

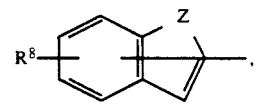

and

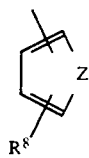

where Z is selected from oxygen, sulfur and —NR$^9$, with the proviso that when A is

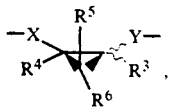

then Ar is

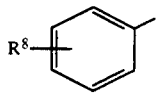

R$^7$ is selected from the group consisting of alkyl, cycloalkyl, carbocyclic aryl, carbocyclic aralkyl, heterocyclic aryl, and heterocyclic aralkyl.

R$^8$ is one, two, or three substituents independently selected from the group consisting of halogen, cyano, hydroxy, alkyl, halosubstituted alkyl, alkenyl, alkoxy, alkoxyalkyl, alkoxyalkoxyalkyl, cycloalkyl, carbocyclic aryl, carbocyclic aryloxy, carbocyclic aroyl, carbocyclic aralkyl, carbocyclic aralkenyl, carbocyclic aralkoxy, carbocyclic arylthioalkoxy, carbocyclic aralkoxyalkyl, carbocyclic arylthioalkoxyalkyl, heteroaryl, and heteroarylalkyl.

R$^8$ may also be further substituted with a radical selected from the group consisting of halo, cyano, alkyl, alkoxy, halosubstituted alkyl, —(CH$_2$)$_p$C(O)R$^{10}$, and —(CH2)$_p$NHC(O)R$^{10}$ where p is zero or is an integer of from one to eight and R10 is selected from the group consisting of alkyl, alkoxy, amino, alkylamino, dialkylamino, and carbocyclic aryl.

R$^9$ is selected from the group consisting of hydrogen, alkyl, carbocyclic aralkyl, heteroarylalkyl, alkoyl, carbocyclic aroyl, and heteroaroyl.

The groups R$^1$ and R$^2$ are independently selected from hydrogen, substituted alkyl, substituted carbocyclic aralkyl, and substituted cycloalkyl wherein the substituents are selected from the group consisting of alkoxy, halo, cyano, amino, carboxyl, hydroxy, —C(O)R$^{10}$, —OC(O)R$^{10}$, and —NHC(O)R$^{10}$ where R$^{10}$ is selected from the group consisting of alkyl, alkoxy, amino, alkylamino, dialkylamino, and carbocyclic aryl.

M is selected from hydrogen, a pharmaceutically acceptable cation, and a pharmaceutically acceptable metabolically cleavable group.

Also contemplated as falling within the scope of the present invention are the pharmaceutically acceptable acid addition salts of the above compounds.

In other aspects of the present invention, there are also provided pharmaceutical compositions and methods of inhibiting lipoxygenase enzymes and related disorders comprising the administration to a mammal, preferably a human, in need of such treatment of a compound of Formula I.

DETAILED DESCRIPTION AND PREFERRED EMBODIMENTS

As used throughout this specification and the appended claims, the following terms have the definitions indicated.

The term "alkyl" refers to straight and branched chain saturated hydrocarbon radicals having 1 to 12 carbon atoms. Representative examples of such radicals are methyl, ethyl, n-propyl, isopropyl, n-butyl, sec-butyl, isobutyl, tert-butyl, and the like.

The term "alkenyl" as used herein refers to straight and branched chain hydrocarbon radicals having 2 to 12 carbon atoms, and containing at least one carbon-carbon double bond. Representaive of such radicals are ethenyl, 1-propenyl, 2-propenyl, 2-methyl-1-propenyl, 1-butenyl, 2-butenyl, and the like.

The term "alkoxy" as used herein refers to an alkyl group as previously defined, attached to the remainder of the parent molecule through an oxygen atom. Representative of such radicals are methoxy, ethoxy, isopropoxy, n-butoxy, sec-butoxy, isobutoxy, tert-butoxy, and the like.

The term "alkoxyalkyl" as used herein refers to an alkoxy group, as previously defined, appended to an alkyl radical including, but not limited to, methoxymethyl, ethoxymethyl, and the like.

The term "alkoxyalkoxyalkyl" as used herein refers to an alkoxy group appended to an alkoxy group which is appended to an alkyl radical including, but not limited to, methoxyethoxymethyl, ethoxyethoxymethyl, and the like.

The term "alkylene" as used herein refers to a divalent straight or branched saturated hydrocarbon chain linking groups having 1 to 6 carbon atoms. Representative of such groups are methylene, ethylene, trimethylene, tetramethylene, 2-methyltrimethylene and 2,2-dimethyltrimethylene.

The term "alkyleneoxyalkylene" as used herein refers to —(CH$_2$)$_m$O(CH$_2$)$_n$— wherein m and n are independently selected from 1 to 6.

The term "oxyalkylene" as used herein refers to —O(CH$_2$)$_m$— wherein m is as previously defined.

The term "alkenylene" as used herein refers to a divalent straight or branched chain containing at least one carbon-carbon double bond of from 2 to 6 carbon atoms. Representative of such groups are ethenylene and propenylene.

The term "carbocyclic aryl" as used herein refers to a substituted or unsubstituted mono or polycyclic aromatic carbocyclic group containing fused or nonfused aromatic ring systems including, but not limited to, phenyl, naphthyl, biphenyl, triphenyl, and the like. Substituents are selected from alkyl, halosubstituted alkyl, alkenyl, hydroxy, halogen, cyano, amino, aminoalkyl, alkylaminoalkyl, dialkylaminoalkyl, and the like.

The term "heteroaryl" as used herein refers to substituted or unsubstituted 5-or 6-membered ring aromatic groups containing one, two or three heteroatoms independently selected from the group consisting of oxygen, sulfur and nitrogen; and also includes bicyclic groups in which the aromatic heterocyclic ring is fused to one or two benzene rings. Representative of such-groups are pyridyl, thienyl, furyl, indolyl, pyrazinyl, isoquinolyl, quinolyl, imidazolyl, pyrrolyl, pyrimidyl, benzofuryl, benzothienyl, carbazolyl, and the like. Substituents are selected from alkyl, halosubstituted alkyl, alkenyl, hydroxy, halogen, cyano, amino, aminoalkyl, alkylaminoalkyl, dialkylaminoalkyl, and the like.

The term "carbocyclic aralkyl" as used herein refers to a carbocyclic aryl group, as previously defined, appended to an alkyl radical including, but not limited to, benzyl, phenylethyl, naphthylmethyl and the like.

The term "carbocyclic aralkenyl" as used herein refers to a carbocyclic aryl group appended to an alkenyl radical including, but not limited to, cinnamyl, phenylpropenyl and the like.

The term "carbocyclic aralkoxy" as used herein refers to a carbocyclic aryl group appended to an alkoxy radical.

The term "thioalkoxy" refers to an alkyl group, as previously defined, attached to the parent molecule through a sulfur atom.

The term "carbocyclic arylthioalkoxy" as used herein refers to a carbocyclic aryl group appended to a thioalkoxy radical including, but not limited to such groups as benzylthiomethoxy and naphthylthiomethoxy.

The term "carbocyclic aralkoxyalkyl" as used herein refers to an carbocyclic aralkoxy group, as previously defined, appended to an alkyl radical including, but not limited to, benzyloxymethyl and the like.

The term "carbocyclic arylthioalkoxyalkyl" as used herein refers to a carbocyclic arylthioalkoxy group, as previously defined, appended to an alkyl radical.

The term "alkoyl" as used herein refers to an alkyl group, as previously defined, attached to the parent molecule through a carbonyl group.

The term "carbocyclic aroyl" as used herein refers to a carbocyclic aryl group, as previously defined, attached to the parent molecule through a carbonyl group.

The term "heteroaroyl" as used herein refers to a heteroaryl group, as previously defined, attached to the parent molecule through a carbonyl group.

The term "carbocyclic aryloxy" as used herein refers to substituted or unsubstituted carbocyclic aryl groups, as previously defined, attached to the parent molecule through an oxygen atom. Representative of such groups are 4-acetylphenoxy, phenoxy, 1-naphthoxy, 2-naphthoxy, and the like.

The term "cycloalkyl" as used herein refers to saturated and unsaturated cyclic or bicyclic radicals having 3 to 8 carbon atoms. Representative of such groups are cyclopropyl, cyclobutyl, cyclopentyl, cyclohexyl, norbornyl, 2-chlorocyclohexyl, and the like.

The terms "halo" and "halogen" as used herein refer to radicals derived from the elements fluorine, chlorine, bromide and iodine.

The term "halosubstituted" refers to a radical as described above substituted with one or more halogens, and which may also be additionally substituted as defined above. Representative of such groups are chloromethyl, trifluoromethyl, 2,2,2-trichloroethyl, 2,2-dichloro-1-hydroxybutyl, and the like.

The term "pharmaceutically acceptable salts" refers to the relatively non-toxic, inorganic or organic acid addition salts and alkaline earth metal salts of the compounds of this invention. These salts can be prepared in situ during the final isolation and purification of the compounds, or by separately reacting the free base with a suitable organic or inorganic acid. Representative salts include the hydrochloride, hydrobromide, sulfate, nitrate, bisulfate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, lauryl sulphate, and the like. Representative alkali or alkaline earth metal sales include sodium, calcium, potassium and magnesium salts, and the like. It will be apparent to those skilled in the art that, depending upon the number of available amino groups for salt formation, the salts of this invention can be per-N-salts.

The term "pharmaceutically acceptable cation" as used herein means a non-toxic cation based on the alkali and alkaline earth metals, such as sodium, lithium, potassium, calcium, magnesium and the like, as well as those based on non-toxic ammonium, quaternary ammonium and amine cations, including but not limited to, ammonium, tetramethylammonium, tetraethylammonium, methylamino, dimethylamino, trimethylamino, triethylamino, and ethylamino cations, and the like.

The term "metabolically cleavable group" refers to groups which can be cleaved from the molecule by metabolic processes and be substituted with hydrogen, a salt, or form a group which yields an active enzyme inhibitor when the cleavable group is removed from the molecule. Examples of metabolically cleavable groups include —COR, —COOR, —CONRR and —CH$_2$OR radicals where R is selected independently at each occurrence from alkyl, carbocyclic aryl or carbocyclic aryl substituted with one or more of alkyl, halogen, hydroxy or alkoxy. Representative metabolically cleavable groups include acetyl, methoxy-carbonyl, benzoyl, tetrahydropyranyl, methoxymethyl and trimethylsilyl groups.

Certain compounds of this invention may exist in optically active forms. The R and S isomers and mixtures thereof, including racemic mixtures as well as the cis and trans isomers and mixtures thereof are contemplated by this invention. Additional asymmetric carbon atoms may be present in a substituent group such as an alkyl group. All such isomers as well as the mixtures thereof are intended to be included in the invention.

The present invention includes one or more of the compounds of Formula I formulated into compositions together with one or more non-toxic pharmaceutically acceptable carriers, adjuvants or vehicles which are collectively referred to herein as carriers, for parenteral injection, for oral administration in solid or liquid form, for rectal administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the abovementioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include powders, sprays and inhalants. The active component is admixed under sterile conditions with a pharmaceutically acceptable carrier and any needed preservatives, buffers or propellants as may be required. Opthalmic formulations, eye ointments, powders and solutions are also contemplated as being within the scope of this invention.

The present compounds can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the lipoxygenase inhibiting compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

SYNTHESIS OF COMPOUNDS

The compounds of this invention can be prepared by the following processes.

Process 1 involves the reaction of a carboxylic acid of the general formula, Ar—A—COOH, where Ar and A are groups as previously defined, with diphenyl-phosphoryl azide (DPPA) in the presence of triethylamine to form the intermediate isocyanate, Ar—A—N=C=O which is subsequently reacted with a hydroxylamine, $NHR_1OM$, where $R_1$ and M are groups as previously defined, to provide the desired hydroxyurea compound.

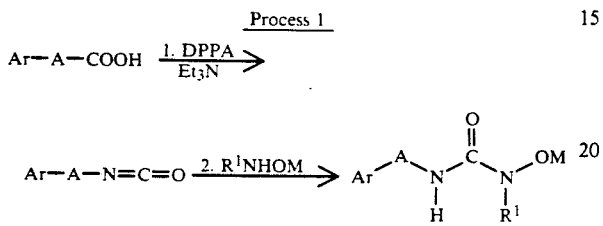

Alternative known methods for the conversion of a carboxylic acid to the corresponding isocyanate can also be employed in the first part of Process 1 such as treatment of the carboxylic acid, Ar—A—COOH with thionyl chloride or oxalyl chloride to provide the corresponding acid chloride, Ar—A—COCl which is then reacted with an azide salt to form the acyl azide intermediate, Ar—A—$CON_3$ which upon heating fragments to provide the isocyanate, Ar—A—N=C=O.

Process 2 involves reductive amination with an amine salt, $H_3NR_1OAc$ effected by sodium cyanoborohydride of a carbonyl precursor, Ar—A(C=O), where a carbonyl function is located on the group A as previously defined to provide the amine intermediate Ar—A—$NHR_1$. This amine is treated with HCl followed by phosgene to provide the isocyanate intermediate which is not isolated but directly treated with a hydroxylamine, $NHR_1OM$ to provide the desired hydroxyurea compound.

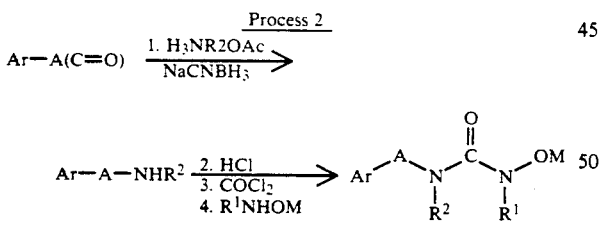

The compounds of formula I above where A is a cyclopropyl ring can be prepared by the following processes.

Process 3 involves the reaction of a cyclopropylcarboxylic acid II, where Ar and X are groups as previously defined, with diphenylphosphorylazide (DPPA) in the presence of triethylamine to form the intermediate isocyanate, III, which is subsequently reacted with a hydroxylamine, $NHR_1OM$ where $R_1$ and M are groups as previously defined, to provide the desired hydroxyurea compound IV.

Alternative known methods for the conversion of a carboxylic acid to the corresponding isocyanate can also be employed in the first part of Process 3 such as treatment of the carboxylic acid, II, with thionylchloride or oxalyl chloride to provide the corresponding acid chloride which is then reacted with an azide salt to form the acyl azide intermediate which upon heating fragments to provide the isocyanate, III.

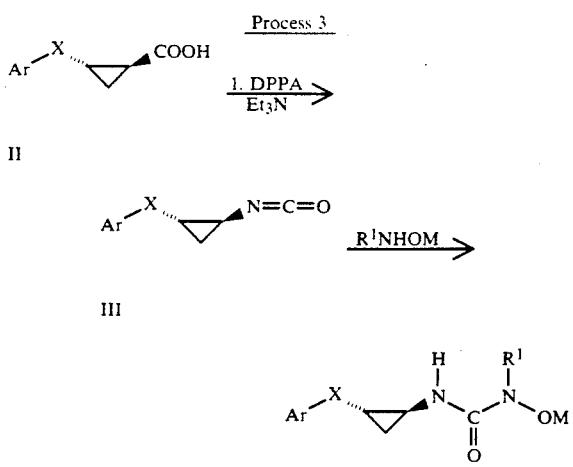

Process 4 involves reductive amination of a cyclopropyl aldehyde or ketone precursor V (where a carbonyl function is located on the group Y as previously defined) with an amine salt, $H_3NR_2OAc$ effected by sodium cyanoborohydride to provide the amine intermediate, VI. This amine is treated with HCl followed by phosgene to provide the isocyanate intermediate which is not isolated but directly treated with a hydroxylamine, $R_1NHOM$ to provide the desired hydroxyurea compound of the present invention.

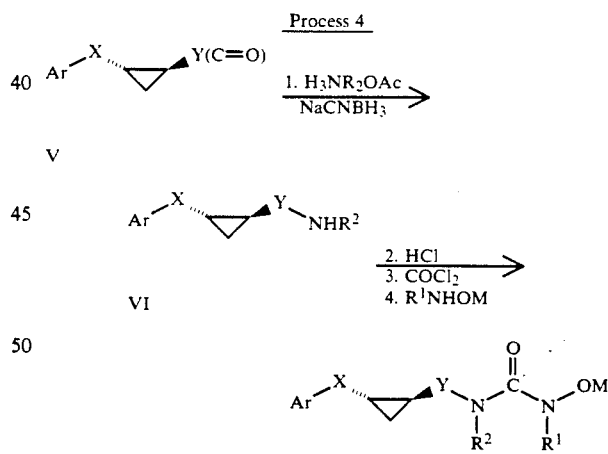

The following examples further illustrate the invention and are not to be construed as limiting of the specification and claims in any way.

EXAMPLE 1

Preparation of N'-hydroxy-N-[1-(phenylmethoxyphenyl)ethyl]urea a. 4-Phenylmethoxyacetophenone. 4-Hydroxyacetophenone (5.0 g, 36.7 mmol) was dissolved in dimethylsulfoxide (50 mL) and potassium t-butoxide (4.73, 42.2 mmol) was added. Twenty minutes later benzyl bromide (7.85 g, 45.8 mmol) was added. After an additional hour, the reaction mixture was poured into water and extracted with ether. The ether layer was dried with magnesium sulfate and evaporated to give the desired material as an off white solid which was used in step (b) without further purification.

b. 1-(4-phenylmethoxyphenyl)ethyl amine. The material prepared in step (a) above (12 g, 53 mmol), ammonium acetate (38 g, 500 mmol), and sodium cyanoborohydride (2.23 g, 35 mmol) were dissolved in methanol (250 mL) and stirred for 3 days. The pH was adjusted to 2.0 with concentrated HCl and the solvent was evaporated. The residue was partitioned between water and ether and the insoluble solids were filtered off and set aside. The water layer was brought to pH 9 with solid $NaHCO_3$ and with 2N NaOH. The now cloudy mixture was extracted with ether. The ether layer was dried over $MgSO_4$ and evaporated. The residue was combined with the solid material collected earlier and this material was used in step (c) without further purification.

c. N'-hydroxy-N-(1-(4-phenylmethoxyphenyl)ethyl urea. The material prepared in step (b) above (4.0 g, 16.4 mmole) was dissolved in 150 mL toluene. HCl gas was bubbled through the solution for 5 minutes resulting in precipitation of the amine hydrochloride. The suspension was heated to 100° C. and phosgene was bubbled through. Within 15 minutes all of the solid dissolved. The phosgene flow was stopped and the solution was heated at reflux for an additional 30 minutes. Most of the toluene was removed by distillation at atmospheric pressure (10 mL final volume). In a separate vessel, hydroxylamine hydrochloride (1.4 g, 20 mmole) was dissolved in water (3 mL) and triethyl amine (2.5 g, 25 mmol) in THF (50 mL) was added. The solution prepared above was then added with vigorous stirring. After being allowed to stir for 30 minutes the mixture was poured into 2N HCl (100 mL) and a precipitate formed. The precipitate was removed by filtration and recrystallized from ethanol to give the desired material.

Melting Point: 164°-165° C.

NMR (300 MHz, DMSO-$d_6$): 1.36 (d, 3H); 4.79 (m, 1H); 5.08 (s, 2H); 6.86 (d, 1H); 6.94 (d, 2H); 7.26 (d, 2H); 7.32-7.47 (m, 5H); 8.31 (s, 1H); 8.60 (s, 1H).

IR (KBr): 3390, 1630, 1550, 1510.

Mass spectrum (CI—$NH_3$): 287 (M+1)+, 304 (M+$NH_4$)+.

EXAMPLE 2

Preparation of
N'-hydroxy-N'-methyl-N-[1-(4-phenylmethoxyphenyl)ethyl]urea

The title compound was prepared according to the procedure of Example 1, substituting N-methylhydroxyl-amine for hydroxylamine.

Melting Point: 105°-106° C.

NMR (300 MHz, DMSO-$d_6$): 1.34 (d,3H); 2.92 (s, 3H); 4.73 (m, 1H); 5.08 (s, 2H); 6.92 (d, 1H); 7.03 (d, 2H); 7.24 (d, 2H); 7.32-7.47 (m, 5H); 9.38 (s, 1H).

Mass spectrum (CI—$NH_3$): 301 (M+1)+, 318 (M+$NH_4$)+, 211, 108, 102.

EXAMPLE 3

Preparation of
N'-hydroxy-N-[1-(4-butoxyphenyl)ethyl]urea

The title compound was prepared according to the procedure of Example 1, substituting 1-bromobutane for benzylbromide.

Melting Point: 125°-127° C.

NMR (300 MHz, DMSO-$d_6$): 0.93 (t, 3H); 1.37 (d, 3H); 1.42 (m, 2H); 1.67 (m, 2H); 3.92 (t, 3H); 4.78 (m, 1H); 6.82 (d, 2H); 6.85 (d, 2H); 7.23 (d, 2H); 8.30 (s, 1H); 8.59 (s, 1H).

IR ($CDCl_3$): 3420, 1650, 1610, 1540, 1510.

Mass spectrum (EI): 252 M+, 235, 177.

EXAMPLE 4

Preparation of
N'-hydroxy-N-[(1-naphth-2-yl)ethyl]urea

The title compound was prepared according to the procedure of Example 1, substituting 2-acetonaphthalene for 4-phenylmethoxyacetophenone.

Melting Point: 156°-157° C.

NMR (300 MHz, DMSO-$d_6$): 1.49 (d, 3H); 5.04 (q, 1H); 7.10 (d, 1H), 7.45-7.58 (m, 3H); 7.80 (s, 1H); 7.83-7.90 (m, 1H); 8.39 (s, 1H); 8.65 (s, 1H).

IR (KBr): 3400, 1640, 1565, 1440.

Mass spectrum (CI—$NH_3$): 231 (M+)+, 248 (M+$NH_4$)+, 172, 170, 155.

EXAMPLE 5

Preparation of
N'-hydroxy-N'methoxy-N-[(1-naphth-2-yl)ethyl]urea

The title compound was prepared according to the procedure of Example 1, substituting 2-acetonaphthalene for 4-phenylmethoxyacetophenone and using methylamine hydrochloride instead of ammonium acetate.

Melting Point: 152°-153° C.

NMR (300 MHz, DMSO-$d_6$): 1.52 (d, 3H); 2.49 (s, 3H); 5.65 (q, 1H); 7.37 (dd, 1H), 7.47-7.94 (m, 7H); 8.10 (s, 1H); 8.98 (s, 1H),

IR (KBr): 1620, 1500, 1480.

Mass spectrum (EI): 244 M+, 227, 155.

EXAMPLE 6

Preparation of
N'-hydroxy-N'-methyl-N-[(thien-2-yl)methyl]urea

To a stirred solution of 2-thiopheneacetic acid (2.00 g, 14.1 mmol) in benzene (70 mL) was added triethylamine (1.424 g, 14.1 mmol) followed by diphenylphosphoryl azide (3.868 g, 14.1 mmol) and the mixture was heated at 90° C. for 1 hour. Then N-methylhydroxylamine hydrochloride (2.36 g, 28.2 mmol) was added as a solution in water (1 mL) containing triethylamine (2.85 g, 28.2 mmol) and the mixture was heated at 90° C. for 18 hours. The reaction was then poured into aqueous saturated $NH_4Cl$ (70 mL) and extracted with ethylacetate (3×70 mL). The combined organic extract was dried over $MgSO_4$ and concentrated. The resulting residue was purified by column chromatography (silica gel, ether-hexanes, 1:1) followed by crystallization in ethylaCetate-hexanes and gave the desired product (467 mg).

Melting Point: 106°-107° C.

NMR (300 MHz, DMSO-$d_6$): 2.96 (s, 3H), 4.36 (d, 2H, J=7 Hz), 6.93 (m, 2H), 7.34 (m, 1H), 7.49 (t, 1H, J=6 Hz), 9.39 (s, 1H)

Mass spectrum (CI—$NH_3$): M+ = 187

Analysis Calc'd for $C_7H_{10}N_2O_2S$: C, 45.14; H, 5.41; N, 15.05; Found C, 45.21; H, 5.27; N, 14.45.

EXAMPLE 7

Preparation of N'-hydroxy-N-[(1-benzofuran-2-yl)ethyl]urea

The title compound was prepared according to the procedure of Example 1, substituting benzofuran-2-yl methyl ketone for 4-phenylmethoxyacetophenone and using O-trimethylsilylhydroxylamine instead of hydroxylamine hydrochloride.

Melting Point: 157°–158° C.

NMR (300 MHz, DMSO-$d_6$): 1.50 (d, 3H, J=7 Hz), 5.07 (m, 1H), 6.67 (m, 1H), 7.02 (d, 1H, J=9 Hz), 7.23 (m, 2H), 7.55 (m, H), 8.51 (d, 1H, J=0.5 Hz), 8.66 (d, 1H, J=1 Hz)

Mass spectrum: M+ =221

Analysis Calc'd for $C_{11}H_{12}N_2O_3$: C, 59.99; H, 5.49; N, 12.72; Found: C, 59.63; H, 5.44; N, 12.66;

EXAMPLE 8

Preparation of N'-hydroxy-N'-methyl-N-[(thienyl-3-yl)methyl]urea

The title compound was prepared according to the procedure of Example 6, substituting 3-thiopheneacetic acid for 2-thiopheneacetic acid.

m.p.=108.5°–109.0° C.

NMR (300 MHz, DMSO-$d_6$): 2.96 (s, 3H), 4.20 (d, 2H, J=6.5 Hz), 7.03 (dd, 1H, J=5.5, 1 Hz), 7.21 (m, 1H), 7.35 (bt, 1H, J=6.5 Hz), 7.44 (dd, 1H, J=5.5, 3 Hz), 9.36 (s, 1H)

Mass spectrum: M+ =187

Analysis Calc'd for $C_7H_{10}N_2O_2S$: C, 45.14; H, 5.41; N, 15.05; Found: C, 45.19; H, 5.34; N, 14.66.

EXAMPLE 9

Preparation of N'-hydroxy-N-[1-(2,5-dimethylthien-3-yl)ethyl]urea

The title compound was prepared according to the procedure of Example 1, substituting 3-acetyl-2,5-dimethyl thiophene for 4-phenylmethoxyacetophenone.

m.p.=124°–126° C.

NMR (300 MHz, DMSO-$d_6$): 1.31 (d, 3H, J=7.5 Hz), 2.29 (s, 3H), 2.32 (s, 3H), 4.83 (m, 1H), 6.71 (d, 1H, J=8.5 Hz), 6.76 (d, 1H, J=1 Hz), 8.28 (d, 1H, J=0.5 Hz), 8.55 (d, 1H, J=1 Hz)

Mass spectrum: M+ =215

Analysis Calc'd for $C_9H_{14}N_2O_2S$: C, 50.44; H, 6.58; N, 13.08; Found: C, 50.41; H, 6.53; N, 13.02.

EXAMPLE 10

Preparation of N'-hydroxy-N'-methyl-N-[(1-benzofur-2-yl)-ethyl]urea

The title compound was prepared according to the procedure of Example 1, substituting benzofuran-2-yl methyl ketone for 4-phenylmethoxyacetophenone and N-methylhydroxylamine hydrochloride for hydroxylamine hydrochloride.

Melting Point: 119.5°–120.5° C.

NMR (300 MHz, DMSO-$d_6$): 1.50 (d, 3H, J=7 Hz), 2.99 (s, 3H), 5.02 (m, 1H), 6.66 (s, 1H), 7.22 (m, 3H), 7.52 (d, 1H, J=8 Hz), 7.58 (m, 1H), 9.45 (s, 1H)

Mass spectrum: M+ =235

Analysis Calc'd for $C_{12}H_{14}N_2O_3$: C, 61.52; H, 6.02; N, 11.96; Found: C, 59.29; H, 5.82; N, 11.43.

EXAMPLE 11

Preparation of N'-hydroxy-N-1-(trans-2-phenylcyclopropyl)urea

The title compound was prepared according to the procedure of Example 6, substituting trans-2-phenyl-1-cyclopropanecarboxylic acid for 2-thiophenecarboxylic acid and O-trimethylsilylhydroxylamine for N-methylhydroxylamine hydrochloride.

m.p.=143.5°–145° C.

NMR (300 MHz, DMSO-$d_6$): 1.08 (m, 1H), 1.26 (m, 1H), 1.95 (m, 1H), 2.73 (m, 1H), 7.00 (d, 1H, J=4 Hz), 7.06–7.29 (m, 5H), 8.38 (s, 1H), 8.56 (s, 1H)

Mass spectrum: M+ =193

Analysis Calc'd for $C_{10}H_{12}N_2O_2$: C, 62.48; H, 6.29; N, 14.58; Found: C, 62.73; H, 6.47; H, 14.55;

EXAMPLE 12

Preparation of N'-hydroxy-N'-(2-hydroxyethyl)-N-[(thien-3-yl)-methyl]urea

The title compound was prepared according to the procedure of Example 6, except using 3-thiopheneacetic acid in place of 2-thiopheneacetic acid and using the oxalate salt of 2-hydroxylaminoethanol, prepared according to Kim, H. K.; Bamburg, R. E.; Yaktin, H. K. J. Med. Chem. 1971, 14, 301, instead of N-methylhydroxylamine hydrochloride.

m.p.=114.5°–115° C.

NMR (300 MHz, DMSO-$d_6$): 3.41 (m, 2H), 3.51 (m, 2H), 4.21 (d, 2H, J=6 Hz), 4.52 (t, 1H, J=6 Hz), 7.04 (dd, 1H, J=5.5 Hz, 1.5 Hz), 7.21 (m, 1H), 7.34 (bt, 1H, J=6.5 Hz), 7.44 (dd, 1H, J=5.5 Hz, 3 Hz), 9.28 (s, 1H)

Mass spectrum: M+ =217

Analysis Calc'd for $C_8H_{12}N_2O_3S$: C, 44.43; H, 5.60; N, 12.96; Found: C, 44.42; H, 5.59; N, 12.73.

EXAMPLE 13

Preparation of N'-hydroxy-N'-methyl-N-[1-(2,5-dimethylthien 3-yl)ethyl]urea

The title compound was prepared according to the procedure of Example 1, except using 3-acetyl-2,5-dimethylthiophene instead of 4-phenylmethoxyacetophenone and using N-methylhydroxylamine hydrochloride instead of hydroxylamine hydrochloride.

m.p.=104.5°–105.5° C.

NMR (300 MHz, DMSO-$d_6$): 1.30 (d, 3H, J=7 Hz), 2.28 (s, 3H), 2.31 (s, 3H), 2.92 (s, 3H), 4.78 (m, 1H), 6.75 (d, 1H, J=1.5 Hz), 6.90 (d, 1H, J=9 Hz), 9.33 (s, 1H)

Mass spectrum: M+ =229

Analysis Calc'd for $C_{10}H_{16}N_2O_S$: C, 52.60; H, 7.06; N, 12.27; Found: C, 52.75; H, 7.06; N, 12.26.

EXAMPLE 14

Preparation of N'-hydroxy-N'-methyl-N-1-(trans-2-phenylcyclopropyl)urea

To a stirred solution of trans-2-phenylcyclopropylcarboxylic acid (3.00 g, 18.5 mmol) in benzene (90 mL) was added triethylamine (1.87 g, 18.5 mmol) followed by diphenylphosphoryl azide (5.10 g, 18.5 mmol) and the mixture was heated at 90° C. for 1 hour. Then N-methylhydroxylamine hydrochloride (3.09 g, 37 mmol) was added as a solution in water (1 mL) containing triethylamine (3.74 g, 37 mmol) and the mixture was heated at 90° C. for 18 hrs. The reaction was then poured into aqueous staturated NH₄Cl (90 mL) and extracted with ethylacetate (3×90 mL). The combined organic extract was dried over MgSO₄ and concentrated. The resulting residue was purified by column chromatography (silica gel, ether) followed by crystallization in ethylacetate-hexanes and gave the desired product (1.79 g).

Melting Point: 113.0°–113.5° C.

NMR (300 MHz, DMSO-$d_6$): 1.08 (m, 1H), 1.25 (penter, 1H), 1.94 (m, 1H), 2.69 (sextet, 1H), 2.95 (s, 3H), 7.07–7.28 (m, 6H), 9.32 (s, 1H)

Mass spectrum: $M^+ = 207$

Analysis Calc'd for $C_{11}H_{14}N_2O_2$: C, 64.06, H, 6.84, N, 13.59; Found: C, 64.18, H, 6.87, N, 13.47.

EXAMPLE 15

Preparation of N'-hydroxy-N'-methyl-N-[1-trans-2-phenylcyclopropyl)ethyl]urea a. A solution of trans-2-phenyl-1-acetylcyclopropane (2.38 g, 14.9 mmol), ammonium acetate (22.93 g, 297.5 mmol) and sodium cyanoborohydride (655 mg, 10.43 mmol) in methanol (60 mL) was stirred for 24 hrs. The pH was adjusted to 2.0 by the addition of concentrated HCl and the solvent was evaporated. The residue was taken up in water (100 mL) and washed with ethylacetate (2×100 mL). The aqueous was then basified to pH 10 by the addition of solid sodium hydroxide, then extracted with ethylacetate (3×100 mL). These last organics were combined, dried with MgSO₄ and concentrated and the resulting material was used without further purification.

b. 1-(Trans-2-phenylcyclopropyl)ethylamine (1.17 g, 7.3 mmol) was taken up in 50 mL saturated methanolic HCl and concentrated. The resulting residue was taken up in toluene (6 mL) and heated to 100° C. A solution of phosgene (37.8 mL of a 1.93M solution in phosgene, 73 mmol) was added slowly. Upon completion of addition, the reaction was brought to reflux for 30 mins. Most of the toluene was removed by distillation at atmospheric pressure leaving a volume of approximately 5 mL. A solution of N-methylhydroxylamine hydrochloride (744 mg, 8.91 mmol) and triethylamine (1.12 g, 11.1 mmol) in THF (25 mL) containing water (1.3 mL) was added dropwise at r.t. The reaction was stirred for 45 mins at room temperature. It was then diluted with 10% aqueous HCl (75 mL) and extracted with ethylacetate (3×75 mL). The organics were combined, dried with MgSO₄ and concentrated. The resulting residue was purified by column chromatography (silica gel, ether-hexanes, 4:1) followed by crystallization in ether-hexanes and gave the desired product (767 mg).

Melting Point: 80°–88° C.

NMR (300 MHz, DMSO-$d_6$, 45:55 ratio of diastereomers): 0.83 and 0.93 (m, 2H), 1.16 and 1.18 (d, 3H, J=7 Hz), 1.26 (m, 1H), 1.79 and 1.89 (m, 1H), 2.93 and 2.95 (s, 3H), 3.30 (m, 1H), 6.76 (m, 1H), 7.03 (m, 2H), 7.11 (m, 1H), 7.23 (m, 2H), 9.32 and 9.37 (s, 1H)

Mass spectrum: $M^+ = 235$

Analysis Calc'd for $C_{13}H_{18}N_2O_2$: C, 66.64, H, 7.74, N, 11.96; Found: C, 66.74, H, 7.79, N, 11.97.

EXAMPLE 16

Preparation of N'-hydroxy-N'-methyl-N-[1-(trans-2-(4-methoxyphenyl)cyclopropyl)methyl]urea The title compound was prepared according to the procedure of Example 15, substituting trans-2-(4-methoxyphenyl) cyclopropanecarboxaldehyde for trans-2-phenyl-1-acetylcyclopropane.

Melting Point: 111.5°–112.5° C.

NMR (300 MHz, DMSO-$d_6$): 0.74 (m, 1H), 0.81 (m, 1H), 1.17 (m, 1H), 1.77 (m, 1H), 2.94 (s, 3H), 3.06 (m, 2H), 3.70 (s, 3H), 6.80 (m, 2H), 6.95 (m, 2H), 7.03 (t, 1H, J=6 Hz), 9.34 (s, 1H)

Mass spectrum: $M^+ = 251$

Analysis Calc'd for $C_{13}H_{18}N_2O_3$: C, 62.38, H, 7.25, N, 11.20; Found: C, 62.41, H, 7.36, N, 11.16.

The compounds represented in Table 1 can be prepared by the method of Process 1 as described in Example 6 by using the appropriate carboxylic acid precursor shown instead of 2-thiopheneacetic acid and using the appropriate hydroxylamine derivative as shown.

TABLE 1

| Carboxylic Acid | Hydroxylamine | Product |
|---|---|---|
| 5-methylfuran-2-CH₂-CO₂H | CH₃NHOH | 5-methylfuran-2-CH₂-C(O)-N(H)-N(OH)(CH₃) |
| 5-phenylfuran-2-CH=CH-CO₂H | CH₃NHOH | 5-phenylfuran-2-CH=CH-C(O)-N(H)-N(OH)(CH₃) |
| 2-methylfuran-3-CH₂-CO₂H | CH₃NHOH | 2-methylfuran-3-CH₂-C(O)-N(H)-N(OH)(CH₃) |
| furan-3-CH₂-CO₂H | CH₃NHOH | furan-3-CH₂-C(O)-N(H)-N(OH)(CH₃) |
| 5-(pyridin-3-yl)furan-2-CH₂-CO₂H | CH₃NHOH | 5-(pyridin-3-yl)furan-2-CH₂-C(O)-N(H)-N(OH)(CH₃) |
| 5-(pyridin-3-yl)-2-methylfuran-3-CH₂-CO₂H | CH₃NHOH | 5-(pyridin-3-yl)-2-methylfuran-3-CH₂-C(O)-N(OH)(CH₃) |

TABLE 1-continued

| Carboxylic Acid | Hydroxylamine | Product |
|---|---|---|
| (5-ethoxymethyl-furan-2-yl)-acetic acid | CH₃NHOH | N-hydroxy-N-methyl-2-(5-ethoxymethyl-furan-2-yl)-acetamide |
| (5-benzyloxymethyl-furan-2-yl)-acetic acid | CH₃NHOH | N-hydroxy-N-methyl-2-(5-benzyloxymethyl-furan-2-yl)-acetamide |
| (5-styryl-furan-2-yl)-acetic acid | CH₃NHOH | N-hydroxy-N-methyl-2-(5-styryl-furan-2-yl)-acetamide |
| (5-phenyl-thiophen-2-yl)-acetic acid | CH₃NHOH | N-hydroxy-N-methyl-2-(5-phenyl-thiophen-2-yl)-acetamide |
| (5-(pyridin-3-yl)-thiophen-2-yl)-acetic acid | CH₃NHOH | N-hydroxy-N-methyl-2-(5-(pyridin-3-yl)-thiophen-2-yl)-acetamide |
| benzo[b]thiophen-3-yl-acetic acid | CH₃NHOH | N-hydroxy-N-methyl-2-(benzo[b]thiophen-3-yl)-acetamide |
| (2,5-dimethyl-thiophen-3-yl)-acetic acid | CH₃NHOH | N-hydroxy-N-methyl-2-(2,5-dimethyl-thiophen-3-yl)-acetamide |

TABLE 1-continued

| Carboxylic Acid | Hydroxylamine | Product |
|---|---|---|
| 5-ethoxy-thiophene-2-CH₂-CO₂H | CH₃NHOH | 5-ethoxy-thiophene-2-CH₂-C(=O)-N(OH)(CH₃) |
| 5-methyl-furan-2-CH₂-O-CH₂CH₂-CO₂H | CH₃NHOH | 5-methyl-furan-2-CH₂-O-CH₂CH₂-C(=O)-N(OH)(CH₃) |
| 5-methyl-furan-2-CH=CH-CO₂H | CH₃NHOH | 5-methyl-furan-2-CH=CH-C(=O)-N(CH₃)(OH) |
| 3-phenoxy-cinnamic acid | CH₃NHOH | 3-phenoxy-cinnamyl-C(=O)-N(OH)(CH₃) |
| 2-(4-phenoxyphenyl)propanoic acid | CH₃NHOH | 2-(4-phenoxyphenyl)-propan-C(=O)-N(OH)(CH₃) |
| 2-(4-benzyloxyphenyl)propanoic acid | CH₃NHOH | 2-(4-benzyloxyphenyl)-propan-C(=O)-N(OH)(CH₃) |

TABLE 1-continued

| Carboxylic Acid | Hydroxylamine | Product |
|---|---|---|
|  | CH₃NHOH |  |
|  | CH₃NHOH |  |
|  | CH₃NHOH |  |
|  | CH₃NHOH |  |
|  | CH₃NHOH |  |

TABLE 1-continued

| Carboxylic Acid | Hydroxylamine | Product |
|---|---|---|
| (3-methoxy-2-furyl styryl α-methyl acetic acid structure) CO₂H | CH₃NHOH | corresponding N-hydroxy-N-methyl amide |
| (N-methylindole styryl acetic acid) CO₂H | CH₃NHOH | corresponding N-hydroxy-N-methyl amide |
| (N-acetylindole styryl acetic acid) CO₂H | CH₃NHOH | corresponding N-hydroxy-N-methyl amide |
| (N-(2-thienylcarbonyl)indole styryl acetic acid) CO₂H | CH₃NHOH | corresponding N-hydroxy-N-methyl amide |
| (5-methyl-2-furyl acetic acid) CO₂H | CH₃O₂C(CH₂)₅NHOH | corresponding N-hydroxy-N-(methyl hexanoate) amide |

TABLE 1-continued

| Carboxylic Acid | Hydroxylamine | Product |
|---|---|---|
| benzothiophene-CH=CH-CO₂H | CH₃O₂C(CH₂)₅NHOH | benzothiophene-CH=CH-C(O)N(OH)(CH₂)₅CO₂CH₃ |
| pyridyl-thiophene-CH=CH-CO₂H | AcO(CH₂)₆NHOH | pyridyl-thiophene-CH=CH-C(O)N(OH)(CH₂)₆OAc |
| 5-methylfuran-CH=CH-CO₂H | PhCH₂NHOH | 5-methylfuran-CH=CH-C(O)N(OH)CH₂Ph |
| 5-methylfuran-CH=CH-CO₂H | NC(CH₂)₅NHOH | 5-methylfuran-CH=CH-C(O)N(OH)(CH₂)₅CN |
| 3-thienyl-CH=CH-CO₂H | (CH₃)₂NC(O)(CH₂)₅NHOH | 3-thienyl-CH=CH-C(O)N(OH)(CH₂)₅CON(CH₃)₂ |
| N-methylpyrrole-CH=CH-CO₂H | CH₃NHOH | N-methylpyrrole-CH=CH-C(O)N(OH)CH₃ |

TABLE 1-continued

| Carboxylic Acid | Hydroxylamine | Product |
|---|---|---|
| | CH$_3$NHOH | |
| | CH$_3$NHOH | |
| | BnNHOH | |
| | BnNHOH | |
| | CH$_3$NHOH | |
| | CH$_3$NHOH | |

TABLE 1-continued

| Carboxylic Acid | Hydroxylamine | Product |
|---|---|---|
| 4-(phenylmethoxy)phenoxyethyl-CO₂H | CH₃NHOH | corresponding N-hydroxy-N-methyl amide |
| 5-(pyridin-3-yl)thiophen-2-yl ethoxy-CO₂H | CH₃NHOH | corresponding N-hydroxy-N-methyl amide |
| 2-[4-(furan-2-ylmethoxy)phenyl]propanoic acid | CH₃NHOH | corresponding N-hydroxy-N-methyl amide |
| CH₃O(CH₂)₂OCH₂-furan-CH₂-CO₂H | CH₃NHOH | corresponding N-hydroxy-N-methyl amide |

The compounds represented in Table 2 can be prepared by the method of Process 2 as described in Example 1 by using the appropriate carbonyl precursor shown instead of 4-phenylmethoxyacetophenone and using the appropriate amine-$R_2$ derivative and hydroxylamine derivative as shown.

The compounds represented in Table 3 can be prepared by the method of Process 3 as described in Example 14 by using the appropriate cyclopropanecarboxylic acid precursor shown instead of trans-2-phenyl-1-cyclopropanecarboxylic acid and using the appropriate hydroxylamine derivative as shown.

TABLE 2

| Carboxylic Acid | Amine | Hydroxylamine | Product |
|---|---|---|---|
| 3-phenoxybenzaldehyde | $H_2N(CH_2)_5CO_2CH_3$ | $CH_3NHOH$ | urea product with $(CH_2)_3CO_2CH_3$ and OH/$CH_3$ |
| 5-methylfuran-2-carbaldehyde | $H_2N(CH_2)_5CO_2CH_3$ | $CH_3NHOH$ | urea product with $(CH_2)_3CO_2CH_3$ and OH/$CH_3$ |
| thiophene-3-carbaldehyde | $H_2NCH_3$ | $CH_3NHOH$ | urea product with $CH_3$ and OH/$CH_3$ |
| (thienyl)vinyl ketone | $H_2N(CH_2)_2OCH_3$ | $CH_3NHOH$ | urea product with $OCH_3$ and OH/$CH_3$ |
| 2-acetylthiophene | $H_2N(CH_2)_4NHCO_2CH_3$ | $CH_3NHOH$ | urea product with $(CH_2)_2NHCO_2CH_3$ and OH/$CH_3$ |
| 4-(1-phenylethoxy)acetophenone | $H_2NCH_3$ | $CH_3NHOH$ | urea product with $CH_3$/$CH_3$ and $CH_3$/OH |

TABLE 3

| Carboxylic Acid | Hydroxylamine | Product |
|---|---|---|
| trans-2-(2-phenoxyphenyl)cyclopropanecarboxylic acid | $CH_3NHOH$ | N-hydroxy-N'-methyl urea of trans-2-(2-phenoxyphenyl)cyclopropylamine |

TABLE 3-continued

| Carboxylic Acid | Hydroxylamine | Product |
|---|---|---|
| PhO-C6H4-cyclopropyl-CO2H | CH3NHOH | PhO-C6H4-cyclopropyl-C(O)N(H)N(CH3)OH |
| benzothiophen-2-yl-cyclopropyl-CO2H | CH3NHOH | benzothiophen-2-yl-cyclopropyl-C(O)N(H)N(CH3)OH |
| (pyridin-4-yloxy)phenyl-cyclopropyl-CO2H | CH3NHOH | (pyridin-4-yloxy)phenyl-cyclopropyl-C(O)N(H)N(CH3)OH |
| (pyridin-2-yloxy)phenyl-cyclopropyl-CO2H | CH3NHOH | (pyridin-2-yloxy)phenyl-cyclopropyl-C(O)N(H)N(CH3)OH |
| (4-chlorophenoxy)phenyl-cyclopropyl-CO2H | CH3NHOH | (4-chlorophenoxy)phenyl-cyclopropyl-C(O)N(H)N(CH3)OH |
| (4-methylphenoxy)phenyl-cyclopropyl-CO2H | CH3NHOH | (4-methylphenoxy)phenyl-cyclopropyl-C(O)N(H)N(CH3)OH |
| (4-methoxyphenoxy)phenyl-cyclopropyl-CO2H | CH3NHOH | (4-methoxyphenoxy)phenyl-cyclopropyl-C(O)N(H)N(CH3)OH |
| (4-methoxyphenoxy)phenyl-cyclopropyl-CO2H | CH3NHOH | (4-methoxyphenoxy)phenyl-cyclopropyl-C(O)N(H)N(CH3)OH |
| naphth-2-yl-cyclopropyl-CO2H | CH3NHOH | naphth-2-yl-cyclopropyl-C(O)N(H)N(CH3)OH |
| 4-(1-phenylethoxy)phenyl-cyclopropyl-CO2H | CH3NHOH | 4-(1-phenylethoxy)phenyl-cyclopropyl-C(O)N(H)N(CH3)OH |
| 4-isopropoxyphenyl-cyclopropyl-CO2H | CH3NHOH | 4-isopropoxyphenyl-cyclopropyl-C(O)N(H)N(CH3)OH |

TABLE 3-continued

| Carboxylic Acid | Hydroxylamine | Product |
|---|---|---|
| 4-bromophenyl-cyclopropane-CO₂H | CH₃NHOH | 4-bromophenyl-cyclopropyl-NHC(O)N(OH)CH₃ |
| 4-methylphenyl-cyclopropane-CO₂H | CH₃NHOH | 4-methylphenyl-cyclopropyl-NHC(O)N(OH)CH₃ |
| 3-thienyl-cyclopropane-CO₂H | CH₃NHOH | 3-thienyl-cyclopropyl-NHC(O)N(OH)CH₃ |
| 2-furyl-cyclopropane-CO₂H | CH₃NHOH | 2-furyl-cyclopropyl-NHC(O)N(OH)CH₃ |
| cyclopropane-CO₂H | CH₃NHOH | cyclopropyl-NHC(O)N(OH)CH₃ |
| 2-bromocyclopropane-CO₂H | CH₃NHOH | 2-bromocyclopropyl-NHC(O)N(OH)CH₃ |
| 2-methoxycyclopropane-CO₂H | CH₃NHOH | 2-methoxycyclopropyl-NHC(O)N(OH)CH₃ |
| 2-benzofuranyl-cyclopropane-CO₂H | CH₃NHOH | 2-benzofuranyl-cyclopropyl-NHC(O)N(OH)CH₃ |
| 1-methylindol-2-yl-cyclopropane-CO₂H | CH₃NHOH | 1-methylindol-2-yl-cyclopropyl-NHC(O)N(OH)CH₃ |
| 2-pyridyl-cyclopropane-CO₂H | CH₃NHOH | 2-pyridyl-cyclopropyl-NHC(O)N(OH)CH₃ |
| 3-(2-thienyloxy)phenyl-cyclopropane-CO₂H | PhCH₂NHOH | 3-(2-thienyloxy)phenyl-cyclopropyl-NHC(O)N(OH)CH₂Ph |
| 5'-methyl-2,2'-bithienyl-5-cyclopropane-CO₂H | AcO(CH₂)₆NHOH | 5'-methyl-2,2'-bithienyl-5-cyclopropyl-NHC(O)N(OH)(CH₂)₆OAc |

Inhibition of 5-Lipoxygenase

The compounds of this invention are potent inhibitors of 5-lipoxygenase. Their activity was determined using the 20,000×g supernatant from homogenized RBL-1 cells in a similar manner as that described by Dyer and coworkers (Dyer, R. D.; Haviv, F.; Hanel, A. M.; Bornemier, D. A.; Carter, G. W. Fed. Proc., Fed. Am. Soc. Exp. Biol. 1984, 43, 1462A). Inhibitory potencies for representative examples of this invention are listed in Table 4. $IC_{50}$ values (concentration of compound producing 50% enzyme inhibition) were calculated by linear regression analysius of percentage inhibition versus log inhibitor concentration plots.

TABLE 4

In Vitro 5-lipoxygenase Inhibitory Activity
Representative Compounds of This Invention

| Example | $IC_{50}$ |
| --- | --- |
| 1 | 1.2 μM |
| 2 | 0.3 μM |
| 3 | 3.8 μM |
| 4 | 4.6 μM |
| 5 | 27.0 μM |
| 6 | 3.6 μM |
| 7 | 12.7 μM |
| 8 | 4.0 μM |
| 9 | 8.4 μM |
| 10 | 0.27 μM |
| 11 | 28.0 μM |
| 12 | 13.0 μM |
| 13 | 0.5 μM |

Inhibition of Leukotriene Biosynthesis In Vivo

Inhibition of the biosynthesis of leukotrienes in vivo after oral administration of compound was determined using a rat peritoneal anaphylaxis model. In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compound was administered by oral gavage one hour prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The results for representative examples of this invention are shown in Table 5.

TABLE 5

In Vivo Inhibition of Leukotriene Biosynthesis by Representative Compounds of This Invention.

| Example | Percent Inhibition With 200 μmol/kg oral dose |
| --- | --- |
| 2 | 86 |
| 6 | 67 |
| 8 | 92 |
| 10 | 50 |
| 12 | 79 |
| 13 | 49 |

We claim:
1. A compound of the formula

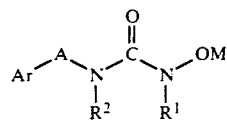

and the pharmaceutically acceptable acid addition salts thereof;

wherein A is a divalent radical selected from the group consisting of alkylene, of from one to six carbon atoms, alkenylene, of from two to twelve carbon atoms, $-(CH_2)_m-O-(CH_2)_n-$ where m and n are independently selected from zero and integers of from one to six, $-O-(CH_2)_m-$ where m is as previously defined Ar is

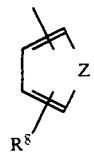

where
Z is sulfur
$R^8$ is one, two, or three substituents independently selected from the group consisting of halogen, cyano, hydroxy, alkyl, halosubstituted alkyl, alkenyl, alkoxy, alkoxyalkyl, alkoxyalkoxyalkyl, cycloalkyl, aryl, aryloxy, aroyl, aralkyl, aralkenyl, aralkoxy, arylthioalkoxy, aralkoxyalkyl, arylthioalkoxyalkyl, heteroaryl, and heteroarylalkyl;

$R^1$ and $R^2$ are independently selected from hydrogen, substituted alkyl, substituted aralkyl, and substituted cycloalkyl wherein the substituents are selected from the group consisting of alkoxy, halo, cyano, amino, carboxyl, hydroxy, $-C(O)R^{10}$, $-OC(O)R^{10}$, and $NHC(O)R^{10}$ where $R^{10}$ is selected from the group consisting of alkyl, alkoxy, amino, alkylamino, dialkylamino, and aryl; and M is selected from hydrogen, a pharmaceutically acceptable cation, and a pharmaceutically acceptable metabolically cleavable group.

2. A compound as defined by claim 1 wherein $R^1$ and $R^2$ are independently selected from substituted alkyl, substituted aralkyl, and substituted cycloalkyl wherein the substituents are selected from the group consisting of alkoxy, halo, cyano, amino, carboxyl, hydroxy, $-C(O)R^{10}$, $-OC(O)R^{10}$, and $-NHC(O)R^{10}$ where $R^{10}$ is selected from the group consisting of alkyl, alkoxy, amino, alkylamino, dialkylamino, and aryl.

3. A compound as defined by claim 1 where M is a metabolically cleavable group selected from the group consisting of aroyl, alkoyl, methoxymethyl, and trimethylsilyl.

4. A compound selected from the group consisting of
N'-hydroxy-N'-methyl-N-[(thien-2-yl)methyl]urea;
N'-hydroxy-N'-methyl-N-[(thienyl-3-yl)methyl]urea;
N'-hydroxy-N-[1-(2,5-dimethylthien-3-yl)ethyl]urea;
N'-hydroxy-N'-[2-hydroxyethyl-N-(thien-3-yl)methyl]urea;
N'-hydroxy-N'-methyl-N-[1-(2,5-dimethylthien-3-yl)ethyl]urea; and pharmaceutically acceptable salts thereof.

5. A pharmaceutical composition for inhibiting lipoxygenase activity in a mammal comprising an effective amount of a compound as defined by claim 1 in combination with a pharmaceutically acceptable carrier.

6. A method of inhibiting lipoxygenase activity in a mammal in need of such treatment comprising administering an effective amount of a compound as defined by claim 1.

* * * * *